(12) United States Patent
Jiang et al.

(10) Patent No.: US 9,139,551 B2
(45) Date of Patent: Sep. 22, 2015

(54) PREPARATION OF A NEW CLASS OF WATER-SOLUBLE AMMONIUM 2,3-DIHYDROXY-5-((2R,3R)-3,5,7-TRIHYDROXY-4-OXOCHROMAN-2-YL) PHENOLATES AND THEIR BIOLOGICAL ACTIVITY OF ALCOHOL ELIMINATION

(71) Applicants: Xianxing Jiang, Lanzhou (CN); Dekui Zhang, Lanzhou (CN); Cheng Jin, Los Angeles, CA (US)

(72) Inventors: Xianxing Jiang, Lanzhou (CN); Dekui Zhang, Lanzhou (CN); Cheng Jin, Los Angeles, CA (US)

(*) Notice: Subject to any disclaimer, the term of this patent is extended or adjusted under 35 U.S.C. 154(b) by 0 days.

(21) Appl. No.: 14/159,588

(22) Filed: Jan. 21, 2014

(65) Prior Publication Data
US 2015/0203465 A1    Jul. 23, 2015

(51) Int. Cl.
| | | |
|---|---|---|
| *A61K 31/445* | (2006.01) | |
| *A61K 31/35* | (2006.01) | |
| *C07D 401/00* | (2006.01) | |
| *C07D 405/00* | (2006.01) | |
| *C07D 409/00* | (2006.01) | |
| *C07D 411/00* | (2006.01) | |
| *C07D 413/00* | (2006.01) | |
| *C07D 417/00* | (2006.01) | |
| *C07D 419/00* | (2006.01) | |
| *C07D 421/00* | (2006.01) | |
| *C07D 311/00* | (2006.01) | |
| *C07D 311/62* | (2006.01) | |

(52) U.S. Cl.
CPC .................................. *C07D 311/62* (2013.01)

(58) Field of Classification Search
None
See application file for complete search history.

(56) References Cited

PUBLICATIONS

Yu, BY. et al. Improving solubility of ampelopsin by solid dispersions and inclusion complexes. Journal of Pharmaceutical and Biomedical Analysis. 2005, vol. 38, p. 457.*

* cited by examiner

*Primary Examiner* — Rita Desai
*Assistant Examiner* — Ben S Michelson
(74) *Attorney, Agent, or Firm* — Jen-Feng Lee, Esq.

(57) ABSTRACT

A new class of high water-soluble compound based upon the *Hovenia* plant, or its herbal extract form known as DHM, and the methods for synthesizing same, to produce anti-alcohol intoxication treatment to alleviate the symptoms of hangover and other over-drinking, binge-drinking related ailments. Such compounds, known as TDHM and PDHM, can reduce the alcohol concentration in the blood, lengthen the waking time, and shorten the period of drowsiness induced after drinking alcohol; they also are proved to have high water solubility and thus are suitable for immediate protection and treatment to persons with alcohol intoxication or hangover and over-drinking.

4 Claims, 1 Drawing Sheet

A: TDHM

B: PDHM

PREPARATION OF A NEW CLASS OF WATER-SOLUBLE AMMONIUM 2,3-DIHYDROXY-5-((2R,3R)-3,5,7-TRIHYDROXY-4-OXOCHROMAN-2-YL) PHENOLATES AND THEIR BIOLOGICAL ACTIVITY OF ALCOHOL ELIMINATION

FIELD AND BACKGROUND OF THE INVENTION

The *Hovenia* plant, and its herbal extract form, has been used as anti-alcohol intoxication treatment to alleviate the symptoms of hangover and other over-drinking, binge-drinking related ailments. It can reduce the alcohol concentration in the blood by enhancing the alcohol dehydrogenase (ADH) and acetaldehyde dehydrogenase (ALHD) activities as well as promoting the protection of liver functions against free radicals.

Studies have shown that the major effective compound of *Hovenia* extracts is dihydromyricetin (DHM), which can promote EtOH elimination via enhancement of alcohol dehydrogenase (ADH) and acetaldehyde dehydrogenase (ALDH) activity. Recent study showed that at cellular level, DHM antagonized both acute EtOH-induced potentiation of GABAARs and EtOH exposure/withdrawal-induced GABAAR plasticity.

In addition to counteracting alcohol intoxication and hepatoprotective property, DHM also possess other properties such as anti-cancer, decreasing blood sugar, anti-inflammation and anti-oxidative.

Despite its therapeutic power, DHM has low water solubility and thus it is not convenient for easy administration of DHM to people in need of immediate anti-intoxication treatment, as well as other ailments that would benefit from the application of DHM, due to its lack of easy water solubility nature.

To overcome the water-solubility issue, present invention synthesized a new class of water-soluble ammonium 2,3-dihydroxy-5-((2R,3R)-3,5,7-trihydroxy-4-oxochroman-2-yl) phenolates; these compounds are named triethylammonium 2,3-dihydroxy-5-((2R,3R)-3,5,7-trihydroxy-4-oxochroman-2-yl)phenolate (TDHM) and piperidinium 2,3-dihydroxy-5-((2R,3R)-3,5,7-trihydroxy-4-oxochroman-2-yl)phenolate (PDHM) respectively, and are proved to have high water solubility and thus are suitable for immediate application and treatment to intoxicated patients.

These compounds were identified by Proton nuclear magnetic resonance and Mass spectroscopy. The PDHM solubility in water reached 5000 mg/L and that of TDHM reached 6500 mg/L.

Compared to the precursor dihydromyricetin (DHM), where the water solubility is no more than 263.54 mg/L, the TDHM and PDHM exhibited an excellent solubility.

The LD50 and MTD of PDHM are 901.57 mg/kg and 3750 mg/kg, respectively; the data figures of TDHM are 748.69 mg/kg and 748.69 mg/kg, respectively. No degeneration and necrosis pathology changes were found in livers, kidneys, hearts and lungs of the mice used in the experiments.

The results indicated that PDHM and TDHM had no significant effect on dietary and body weight in mice. Comparing with control group treated with saline, the results indicated that PDHM and TDHM could significantly decrease the blood alcohol concentration in mice by using a model of the introgastric administration of PDHM and TDHM with 2.0 mg/kg body weight.

BRIEF DESCRIPTION OF THE TABLES AND DRAWINGS

Figure 1:
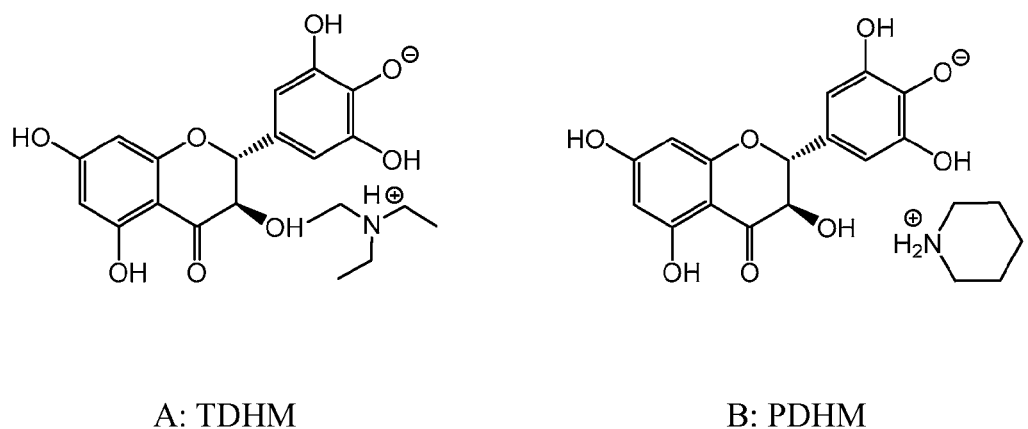
FIG. 1 shows the molecular formula structure of TDHM and PDHM.

Table 1 shows the mortality rate of mice by groups with varied concentration of TDHM.

Table 2 shows average body weight of mice changes by day on variety of concentration of TDHM Table 3 shows dietary changes by day on variety of TDHM concentration.

Table 4 shows dietary change by day at MTD (Maximum Tolerance Dosage) of TDHM.

Table 5 shows average body weight of mice changes by day at MDT of TDHM.

Table 6 shows the mortality rate by groups with varied concentration of PDHM.

Table 7 shows average body weight of mice changes by day on variety of concentration of PDHM.

Table 8 shows dietary changes by day on variety of PDHM concentration.

Table 9 shows dietary change by day at MTD of PDHM.

Table 10 shows average body weight of mice changes by day at MDT of PDHM.

Table 11 shows the relative de-intoxication effect of DHM, TDHM and PDHM.

Table 12 shows the relative anti-alcoholism effect of DHM, TDHM and PDHM.

Table 13 shows the climbing tests result, in groups administered by DHM, TDHM and PDHM, respectively.

Table 14 shows the Dose-Effect relationship of anti-alcoholism and climbing ability of TDHM.

DETAILED DESCRIPTION OF PREFERRED EMBODIMENT

To synthesize the compound of TDHM, the follow steps are taken:
  a. At room temperature, form a solution by dissolving 3.2 g, 10.0 mmol of the compound (2R,3R)-3,5,7-trihydroxy-2-(3,4,5-trihydroxyphenyl) chroman-4-one in 20.0 mL MeOH;
  b. Stir said solution for 30 minutes at room temperature and then cool to 0° C. in an ice bath;
  c. Add a second solution of triethylamine (1.2 g, 12.0 mmol) in MeOH (5.0 mL), dropwise at 0° C.;
  d. Wait approximately 25 minutes after the completion of the second solution is added, filter the precipitated white solid by cool-washing with MeOH to produce pure white solid in the amount of 3.4 g, at 81% yield.

To synthesize the compound of PDHM, the follow steps are taken:
  a. At room temperature, form a solution by dissolving 3.2 g, 10.0 mmol of the compound (2R,3R)-3,5,7-trihydroxy-2-(3,4,5-trihydroxyphenyl) chroman-4-one in 20.0 mL MeOH;
  b. Stir said solution for 30 minutes at room temperature and then cool to 0° C. in an ice bath;
  c. Add a second solution of piperidine (0.94 g, 11.0 mmol) in MeOH (5.0 mL), dropwise at 0° C.;
  d. Wait approximately 20 minutes after the completion of the second solution is added, filter the precipitated white solid by cool-washing with MeOH to produce pure white solid of 3.3 g, at 83% yield.

To confirm the efficacy, safety, toxicity and applicability of TDHM/PDHM, applicants used lab mice to conduct extensive experiments and analysis. All mice were allowed to acclimate to the laboratory and test settings for 5-7 days before the confirmation experiments were conducted. The experiments conform to the standards known in the industry to evaluate the effectiveness and validity of the compounds; the experiments done by the applicants are believed to comply with all ethics standards.

The equipment used for analysis and confirmation of the chemical identification and reaction included proton nuclear magnetic resonance ($^1$H NMR and $^{13}$C NMR) spectrometer (Brucker 400 MHz spectrometer) and Mass spectroscopy.

The results are stated summarily herein.

Acute Toxicity

Compounds PDHM/TDHM. Drug dissolution system: dry compound+5% DMSO+5% castor oil+90% saline(V/V). The experiments used two delivery methods: intraperitoneal injection and intragastric administration. At different concentrations of the compounds PDHM/TDHM, mice were observed manifestations of acute poisoning and death, as well as the pathological changes of main organs. Changes in dietary and body weight are observed every day.

Plasma EtOH Concentration Assay.

Blood samples from the tail vein of mice at different time points (0, 15, 30, 45, 60, 90, 120, 240, 480 and 720 minutes) after EtOH (30% ethanol, 0.2 ml/kg bw) or TDHM (2 mg/kg bw), PDHM (2 mg/kg bw) or DHM (2 mg/kg bw) gavage were collected for plasma EtOH concentrations (plasma [EtOH]) assays. ("BW" or "bw": body weight)

Briefly, the Balb/C mice were put into a restraint tube and the tail was warmed at 37° C. The tail vein at the tip of the tail was punched with a sharp blade. Approximately 0.2 ml venous blood was dropped to a capillary blood collection tube containing lithium heparin (Ram Scientific). Blood samples were centrifuged at 2500 rpm for 20 min. The supernatant was collected and stored at −80° C. until assay. The EtOH content of each blood sample was measured in duplicate along with EtOH standards using the alcohol oxidase reaction procedures (EnzyChrom™ Ethanol Acid Assay Kit, ECET-100) (Liang et al., 2007). The sample preparations were the same as described above.

Deintoxication Test

80 Balb/C mice (male:female=1:1) were randomly divided into four groups with 20 mice in each group: Normal group, DHM group, TDHM group, PDHM group. After fasted for 12 hours, then mice in normal group were gavaged saline 0.2 ml/10 kg BW, while mice in PDHM, TDHM, DHM group were gavaged corresponding dosage of 2 mg/kg BW. 30 minutes later, all mice were gavaged with 30% ethanol 0.2 ml/kg bw. Then durations between alcohol intake and intoxication (tolerance time), intoxication and recovery (maintenance time) were recorded.

Anti-Alcoholism Tests

Groups design and treatment before experiment are as the same as that in Deintoxication test. All mice administrated alcohol (liquid Erguotou, ethonol concentration was diluted to 30%) 0.2 ml/kg BW. 30 minutes later mice in normal group were gavaged saline 0.2 ml/10 kg BW, mice in PDHM, TDHM, DHM group were gavaged corresponding dosage of 2 mg/kg BW. Then durations between alcohol intake and intoxication (tolerance time), intoxication and recovery (maintenance time) were recorded.

Climbing Net Test

Groups design and treatment before experiment are as the same as that in deintoxication test. Mice in normal group were gavaged saline 0.2 ml/10 kg BW, mice in PDHM, TDHM, DHM group were gavaged corresponding dosage of 2 mg/kg BW. 30 minutes later all mice administrated alcohol (liquid Erguotou, ethonol concentration was diluted to 30%) 0.2 mL/kg BW and placed on a vertical metal net and measured the time when mice climbed on net.

Assay the Dose-Effect Relationship of TDHM

Groups design and treatment before experiment are the same as that in Deintoxication test. 30 minutes before intragastric administration of alcohol, mice were gavaged with 0.5 mg/kg BW, 2.0 mg/kg BW, 8.0 mg/kg BW, 32 mg/kg BW, 64 mg/kg BW, 128 mg/kg BW TDHM respectively. Sleep time and climbing time were recorded.

Statistical Analysis

Values are mean±SEM. Comparisons were performed by one-way analysis of variance (ANOVA), followed by Tukey's post hoc test. Differences were considered statistically significant when the calculated P value was less than 0.05.

The molecular formula and structure of TDHM and PDHM are identified and confirmed.

Identification of TDHM $^1$H NMR (400 MHz, [D$^6$]DMSO): δ 6.40 (s, 2H), 5.78-5.82 (d, J=16 Hz, 2H), 4.86-4.88 (d, J=8 Hz, 1H), 4.37-4.39 (d, J=8 Hz, 1H), 2.51-1.58 (m, 6H), 0.97-1.00 (t, J=8 Hz, 9H). $^{13}$C NMR (100 MHz, [D$^6$]DMSO): δ 197.1, 170.0, 163.9, 162.9, 146.1, 133.9, 127.7, 107.4, 100.1, 95.9, 83.6, 72.1, 46.1, 11.6.

HRMS-ESI (m/z): calcd for $C_{15}H_{12}O_8$+H$^+$: 321.0610; found: 321.0598, 2.0 ppm.

Solubility of TDHM is 6500 mg/L in water on room temperature.

Identification of PDHM $^1$H NMR (400 MHz, [D$^6$]DMSO): δ 6.38 (s, 2H), 5.59-5.63 (d, J=16 Hz, 2H), 4.76-4.78 (d, J=8 Hz, 1H), 4.28-4.30 (d, J=8 Hz, 1H), 2.83 (br, 4H), 1.52-1.54 (m, 6H). $^{13}$C NMR (100 MHz, [D$^6$]DMSO): δ 195.1, 174.5, 164.1, 162.7, 133.9, 133.3, 128.1, 107.3, 98.5, 98.0, 97.2, 83.4, 71.9, 45.4, 24.6, 23.5.

HRMS-ESI (m/z): calcd for $C_{15}H_{12}O_8$+H$^+$: 321.0610; found: 321.0598, 2.0 ppm.

Solubility of PDHM is 5000 mg/L in water on room temperature

The molecular formula is shown below:

A: TDHM

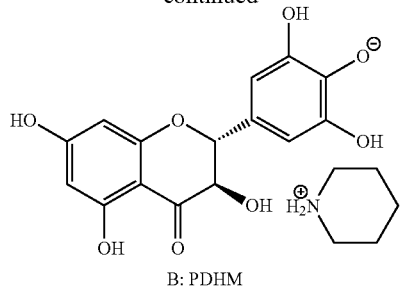

B: PDHM

The Acute Toxicity of TDHM and PDHM

For PDHM

Intraperitoneal Administration(i.p)

140 mice were divided into 7 groups (n=20), each group include 10 males and 10 females, they were treated with different concentrations of dosages and observed for 7 days. Specific experimental groups and experimental results were noted below. Note: Section 1-6 group compound are PDHM groups, and group 7 is a negative control group.

Mice death situations: calculated by the formula (1), the $LD_{50}$ of compound PDHM was 901.57 mg/kg; calculated by the formulas (2) and (3), the 95% confidence limit of LD50 was 742.68-754.74 mg/kg.

(1) $LD_{50}$ was 888.79-914.58 mg/kg.

(2) $S_{x50} = i\sqrt{\Sigma_n^{pq}}$ (3) 95% confidence limit of $LD_{50} = lg^{-1}(lgLD50 \pm 1.96 S_{x50})$

TABLE 1 effect of variety concentration TDHM on mortality of mice

| group | dose (mg/kg) | Dead number | mortality (%) |
|---|---|---|---|
| 1 | 636 | 0 | 0 |
| 2 | 674.16 | 4 | 20 |
| 3 | 714.61 | 4 | 20 |
| 4 | 757.49 | 8 | 40 |
| 5 | 802.94 | 18 | 90 |
| 6 | 851.11 | 20 | 100 |
| 7 | 0 | 0 | 0 |

Notice: group 1-6 variety concentration TDHM group; group 7 negative control group

TABLE 2 effect of variety concentration TDHM on average body weight of mice (g)

| group | dose (mg/kg) | D1 | D2 | D3 | D4 | D5 | D6 | D7 |
|---|---|---|---|---|---|---|---|---|
| 1 | 636 | 0.67 | 1.4 | 2.62 | 3.63 | 5.57 | 5.89 | 6.59 |
| 2 | 674.16 | 1.43 | 2.62 | 3.42 | 4.47 | 6.17 | 6.49 | 7.36 |
| 3 | 714.61 | 1.19 | 2.58 | 3.98 | 5.12 | 6.54 | 7.14 | 7.46 |
| 4 | 757.49 | 0.59 | 1.94 | 3.27 | 4.75 | 6.29 | 7.41 | 7.94 |
| 5 | 802.94 | 0.46 | 1.68 | 2.48 | 3.73 | 5.26 | 5.17 | 5.04 |
| 6 | 851.11 | 0 | 0 | 0 | 0 | 0 | 0 | 0 |
| 7 | 0 | 1.65 | 2.57 | 4.05 | 5.53 | 6.73 | 7.63 | 8.38 |

Notice: group 1-6 variety concentration TDHM group; group 7 negative control group

TABLE 3 effect of variety concentration TDHM on average dietary of mice (g)

| group | dose (mg/kg) | D1 | D2 | D3 | D4 | D5 | D6 | D7 |
|---|---|---|---|---|---|---|---|---|
| 1 | 636 | 3.62 | 4.67 | 5.33 | 6.4 | 5.53 | 5.18 | 5.44 |
| 2 | 674.16 | 3.96 | 4.8 | 6.7 | 6.98 | 5.58 | 5.58 | 5.73 |
| 3 | 714.61 | 3.62 | 5.42 | 6.55 | 7.06 | 5.49 | 5.17 | 5.2 |
| 4 | 757.49 | 3.95 | 5.3 | 7.08 | 8.18 | 5.78 | 5.83 | 6.25 |
| 5 | 802.94 | 4.6 | 7.66 | 7.08 | 9.04 | 6.89 | 6.23 | 6.27 |
| 6 | 851.11 | 0 | 0 | 0 | 0 | 0 | 0 | 0 |
| 7 | 0 | 4.76 | 4.9 | 5.25 | 6.64 | 5.07 | 5.56 | 5.65 |

Notice: group 1-6 variety concentration TDHM group; group 7 negative control group Intragastric Administration(i.g)

In preliminary experiments, applicants used the different compounds PDHM dose gavage once and observed 7 days. During the observation period, no deaths occurred; applicants further enhanced the concentration of the compound PDHM until the appearance of insoluble precipitate, and cannot be completely dissolved in physiological saline, and having reached the maximum mice dosing volume by oral gavage. Thereafter, mice orally maximum tolerated dose (MTD) was measured.

Take 10 mice, 5 male and 5 female respectively, with the greatest volume of dissolved dosage concentration dose (1250 mg/kg) administered three times a day (7 a.m., 12 a.m., 5 p.m.), observe 7 days. No deaths during the observation period. Oral gavage MTD=1250 mg/kg×3=3750 mg/kg. At the end of observation period, the mice were sacrificed, dissection of stomach, liver, kidney for pathological examination and was found to contain no obvious degeneration, necrosis and other changes.

TABLE 4 effect of MTD of TDHM on average dietary of mice (g)

| group | dose (mg/kg) | D1 | D2 | D3 | D4 | D5 | D6 | D7 |
|---|---|---|---|---|---|---|---|---|
| 1 | 2550 | 5.85 | 6 | 5.04 | 5.19 | 4.64 | 4.68 | 5.22 |
| 2 | 0 | 4.98 | 5.21 | 5.37 | 5.82 | 6.03 | 5.94 | 5.71 |

Notice: group 1 TDHM group; group 2 negative control group

TABLE 5 effect of MTD of TDHM on average body weight of mice (g)

| group | dose (mg/kg) | D1 | D2 | D3 | D4 | D5 | D6 | D7 |
|---|---|---|---|---|---|---|---|---|
| 1 | 2550 | 0.98 | 2.1 | 4.1 | 5.51 | 6.52 | 7.51 | 8.34 |
| 2 | 0 | 0.39 | 2.18 | 3.34 | 4.63 | 6.6 | 7.05 | 8.55 |

Notice: group 1 TDHM group; group 2 negative control group

For TDHM

Intraperitoneal Administration(i.p)

140 mice were divided into 7 groups (n=20), each group include 10 males and 10 females, they were treated with different concentrations of dosage and observed for 7 days. Specific experimental groups and experimental results were shown below. Note: Section 1-6 group compound are PDHM groups, and group 7 is a negative control group.

Mice death situations: calculated by the formula (1), the LD50 of compound PDHM was 748.69 mg/kg; calculated by the formulas (2) and (3), the 95% confidence limit of LD50 was 742.68-754.74 mg/kg.

TABLE 6 effect of variety concentration PDHM on mortality of mice

| group | dose (mg/kg) | Dead number | mortality (%) |
|---|---|---|---|
| 1 | 853.27 | 0 | 0 |
| 2 | 874.6 | 6 | 30 |
| 3 | 896.47 | 10 | 50 |
| 4 | 918.88 | 12 | 60 |
| 5 | 941.85 | 18 | 90 |
| 6 | 965.4 | 20 | 100 |
| 7 | 0 | 0 | 0 |

Notice: group 1-6 variety concentration PDHM group; group 7 negative control group

TABLE 7 effect of variety concentration PDHM on average body weight of mice (g)

| group | dose (mg/kg) | D1 | D2 | D3 | D4 | D5 | D6 | D7 |
|---|---|---|---|---|---|---|---|---|
| 1 | 853.27 | 1.34 | 2.02 | 3.36 | 4.67 | 6.13 | 6.68 | 6.91 |
| 2 | 874.6 | 1.12 | 2 | 3.59 | 5.26 | 6.22 | 6.37 | 7.06 |
| 3 | 896.47 | 0.26 | 1.41 | 2.85 | 3.9 | 4.69 | 6.01 | 7.25 |
| 4 | 918.88 | 0.35 | 2.57 | 3.38 | 4.05 | 5.91 | 7.3 | 7.59 |
| 5 | 941.85 | 1.12 | 2.84 | 3.69 | 4.89 | 5.57 | 6.86 | 8.05 |
| 6 | 965.4 | 0 | 0 | 0 | 0 | 0 | 0 | 0 |
| 7 | 0 | 1.65 | 2.57 | 4.05 | 5.53 | 6.73 | 7.63 | 8.38 |

Notice: group 1-6 variety concentration PDHM group; group 7 negative control group

TABLE 8 effect of variety concentration PDHM on average dietary of mice (g)

| group | dose (mg/kg) | D1 | D2 | D3 | D4 | D5 | D6 | D7 |
|---|---|---|---|---|---|---|---|---|
| 1 | 853.27 | 3.79 | 4.58 | 3.6 | 4.92 | 5.76 | 5.31 | 5.83 |
| 2 | 874.6 | 3.91 | 4.73 | 5.81 | 5.43 | 4.97 | 5.88 | 5.72 |
| 3 | 896.47 | 3.35 | 4.92 | 5.78 | 6.04 | 5.72 | 5.34 | 5.65 |
| 4 | 918.88 | 4.21 | 4.79 | 5.21 | 6.08 | 5.83 | 6.24 | 5.13 |
| 5 | 941.85 | 4.76 | 3.92 | 4.66 | 5.82 | 6.15 | 5.79 | 5.43 |
| 6 | 965.4 | 0 | 0 | 0 | 0 | 0 | 0 | 0 |
| 7 | 0 | 4.76 | 4.9 | 5.25 | 6.64 | 5.07 | 5.56 | 5.65 |

Notice: group 1-6 ariety concentration PDHM group; group 7 negative control group Intragastric Administration(i.g)

In preliminary experiment, applicants used the different compounds PDHM dose gavage once and observed for 7 days. During the observation period, no deaths occurred; applicants further enhanced the concentration of the compound PDHM until the appearance of insoluble precipitate, which cannot be completely dissolved in physiological saline, and having reached the maximum mice dosing volume by oral gavage. Thereafter, mice oral maximum tolerated dose (MTD) test was measured.

Take 10 mice, 5 males and 5 females respectively, with the greatest volume of dissolved drug concentration dose (1250 mg/kg) administered three times a day (7 a.m., 12 a.m., 5 p.m.), observe for 7 days. No deaths were found during the observation period. Oral gavage MTD=850 mg/kg×3=2550 mg/kg. At end of the observation period, the mice were sacrificed, dissection of stomach, liver, kidney for pathological examination found no obvious degeneration, necrosis and other changes.

TABLE 9 effect of MTD of PDHM on dietary change-by-day of mice (g)

| group | dose (mg/kg) | D1 | D2 | D3 | D4 | D5 | D6 | D7 |
|---|---|---|---|---|---|---|---|---|
| 1 | 3750 | 5.98 | 6.1 | 6.03 | 6.14 | 6.48 | 6.32 | 6.57 |
| 2 | 0 | 4.98 | 5.21 | 5.37 | 5.82 | 6.03 | 5.94 | 5.71 |

Notice: group 1 PDHM group; group 2 negative control group

TABLE 10 effect of MTD of PDHM on average body weight of mice (g)

| group | Dose (mg/kg) | D1 | D2 | D3 | D4 | D5 | D6 | D7 |
|---|---|---|---|---|---|---|---|---|
| 1 | 3750 | 1.97 | 3.47 | 4.77 | 6.37 | 7.38 | 8.41 | 9.67 |
| 2 | 0 | 0.39 | 2.18 | 3.34 | 4.63 | 6.6 | 7.05 | 8.55 |

Notice: group 1 PDHM group; group 2 negative control group

TDHM, PDHM Decrease the Blood Alcohol Concentration

Figure 2:
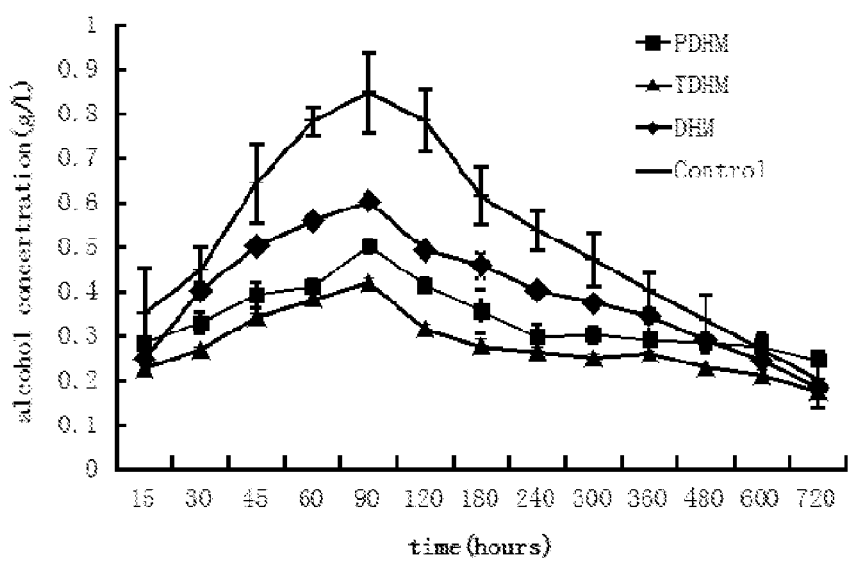
FIG. 2 shows mice BAC (Blood Alcohol Concentration) changes after application of TDHM and PDHM.

As FIG. 2 shows, introgastric administration of DHM, PDHM, TDHM with 2 mg/kg significantly decreased the blood alcohol concentration in mice comparing with control group treated with saline. Among the three compounds, TDHM and PDHM show better beneficial effect than DHM while TDHM is the best in reducing blood alcohol concentration at the same time point. And the results also show the peak time point of alcohol concentration is between 60-90 minutes after administration alcohol.

Anti-Alcoholism Tests of TDHM, PDHM

As table 11 showed, intragastric administration of agents 30 minutes before drinking, TDHM and PDHM obviously prolonged the tolerance time of righting reflex disappearing in mice (P<0.01) and shorten the holding time comparing with DHM, while TDHM is superior to PDHM.

TABLE 11

The results of deintoxication effect of DHM, TDHM, PDHM

| group | number piece | Dead number piece | Rate of drunk % | Tolerance time (min) M ± SD | Sleep time (min) M ± SD |
|---|---|---|---|---|---|
| Normal group | 20 | 2 | 10% | 20.67 ± 7.19 | 179.11 ± 43.46 |
| TDHM G | 20 | 0 | 0 | 43.29 ± 23.44[#] | 69.29 ± 48.40[#] |
| PDHM G | 20 | 2 | 10% | 25.43 ± 10.80[#]* | 125.33 ± 33.75[#]* |
| DHM G | 20 | 2 | 10% | 25 ± 7.29[#]* | 135.71 ± 25.25[#]* |

[#]show vs model group p < 0.05, *show vs TDHM group p < 0.01

Deintoxication Tests of TDHM, PDHM

As table 12 show, TDHM and PDHM remarkably shorten the sleep time in drunk mice comparing with DHM (p<0.05) while no significant difference between TDHM and PDHM (p>0.05).

TABLE 12

The results of anti-alcoholism effect of DHM, TDHM, PDHM

| Group | number piece | Dead number piece | Rate of drunk % | Tolerance time (min) M ± SD | Sleep time (min) M ± SD |
|---|---|---|---|---|---|
| Normal G | 20 | 2 | 10% | 20.67 ± 7.19[#] | 179.11 ± 43.46 |
| TDHM G | 20 | 0 | 0 | 26.28 ± 17.49 | 99.29 ± 19.23*[&] |

TABLE 12-continued

The results of anti-alcoholism effect of DHM, TDHM, PDHM

| Group | number piece | Dead number piece | Rate of drunk % | Tolerance time (min) M ± SD | Sleep time (min) M ± SD |
|---|---|---|---|---|---|
| PDHM G | 20 | 2 | 10% | 22.14 ± 15[#] | 107.71 ± 36.87[*&] |
| DHM G | 20 | 0 | 0 | 18.29 ± 10.07[#] | 138.17 ± 33.73[*] |

[#]show vs TDHM group p < 0.05, [*]show vs model group p < 0.05, [&]show vs DHM group p < 0.05

Climbing Tests

AS table 13 showed, TDHM, PDHM and DHM significantly prolonged the climbing time than normal control mice ($p<0.01$) while TDHM is superior to PDHM and DHM ($p<0.01$), and PDHM is superior to DHM ($p<0.05$).

TABLE 13

The results of climb nets tests in mice

| group | number | climbing (min) |
|---|---|---|
| Model group | 20 | 205.67 ± 65.82 |
| TDHM group | 20 | 471.5 ± 155.89[#*] |
| PDHM group | 20 | 392.25 ± 76.67[#&] |
| DHM group | 20 | 329.75 ± 76.46[#] |

[#]show vs model group p < 0.05,[*]show vs PDHM group p < 0.01, [&]show vs DHM group p < 0.05

Assay the Relationship Between Concentration and Anti-Alcoholic Effect of TDHM

As show the Table 14, after intragastric administration of 8.0 mg/kg BW TDHM drunk mice have a significantly shorter sleep time and longer climbing time than administration of other concentration TDHM.

TABLE 14

Dose-effect relationship of anti-alcoholism and climbing ability of TDHM

| group | 0.5 mg/kg | 2 mg/kg | 8 mg/kg | 32 mg/kg | 64 mg/kg | 128 mg/kg |
|---|---|---|---|---|---|---|
| Climbing time (min) | 184.5 ± 55.42* | 272.67 ± 49.00* | 368.33 ± 112.68 | 243.17 ± 38.03* | 271.83 ± 106.02* | 298.33 ± 98.86* |
| Holding time (min) | 147.2 ± 31.13* | 151.00 ± 43.33* | 104.5 ± 43.08 | 106.67 ± 40.08 | 84.33 ± 32.67* | 93.5 ± 2.12 |

*show vs 8.0 mg/kg BW p < 0.05

The invention claimed is:

1. A triethylammonium 2,3-dihydroxy-5-((2R,3R)-3,5,7-trihydroxy-4-oxochroman-2-yl)phenolate compound having the structural formula of

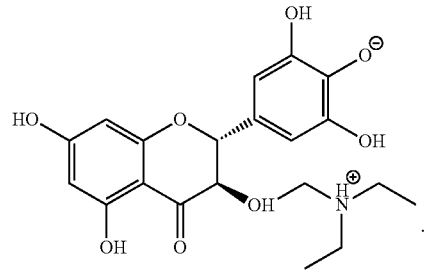

2. The method of synthesizing the compound of claim 1, comprising the steps of:
 a. At room temperature, form a solution by dissolving 3.2 g, 10.0 mmol of the compound (2R,3R)-3,5,7-trihydroxy-2-(3,4,5-trihydroxyphenyl) chroman-4-one in 20.0 mL MeOH;
 b. Stir said solution for 30 minutes at room temperature and then cool to 0° C. in an ice bath;
 c. Add a second solution of triethylamine (1.2 g, 12.0 mmol) in MeOH (5.0 mL), dropwise at 0° C.;
 d. Wait approximately 25 minutes after the completion of the second solution is added, filter the precipitated white solid by cool-washing with MeOH to produce pure white solid in the amount of 3.4 g, at 81% yield.

3. A piperidinium 2,3-dihydroxy-5-((2R,3R)-3,5,7-trihydroxy-4-oxochroman-2-yl)phenolate compound having the structural formula of

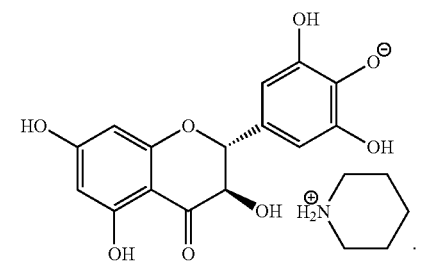 [SMILES: O=C1c2c(O)cc(O)cc2O[C@H](c2cc(O)c([O-])c(O)c2)[C@H]1O ; C1CC[NH2+]CC1]

4. The method of synthesizing the compound of claim 3, comprising the steps of:
 a. At room temperature, form a solution by dissolving 3.2 g, 10.0 mmol of the compound (2R,3R)-3,5,7-trihydroxy-2-(3,4,5-trihydroxyphenyl) chroman-4-one in 20.0 mL MeOH;
 b. Stir said solution for 30 minutes at room temperature and then cool to 0° C. in an ice bath;
 c. Add a second solution of piperidine (0.94 g, 11.0 mmol) in MeOH (5.0 mL), dropwise at 0° C.;
 d. Wait approximately 20 minutes after the completion of the second solution is added, filter the precipitated white solid by cool-washing with MeOH to produce pure white solid of 3.3 g, at 83% yield.

* * * * *